(12) United States Patent
Stensrud

(10) Patent No.: US 9,139,545 B2
(45) Date of Patent: Sep. 22, 2015

(54) DIALLYL ETHERS OF 2,5BIS(HYDROXYMETHYL)TETRAHYDROFURAN AND PROCESSES FOR MAKING THE SAME

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/401,199

(22) PCT Filed: Jun. 10, 2013

(86) PCT No.: PCT/US2013/044875
§ 371 (c)(1),
(2) Date: Nov. 14, 2014

(87) PCT Pub. No.: WO2013/188252
PCT Pub. Date: Dec. 19, 2013

(65) Prior Publication Data
US 2015/0099895 A1 Apr. 9, 2015

Related U.S. Application Data

(60) Provisional application No. 61/658,118, filed on Jun. 11, 2012.

(51) Int. Cl.
*C07D 307/12* (2006.01)
*B01J 31/02* (2006.01)
*C07D 493/04* (2006.01)

(52) U.S. Cl.
CPC ............... *C07D 307/12* (2013.01); *B01J 31/02* (2013.01); *C07D 493/04* (2013.01)

(58) Field of Classification Search
CPC .................................................... C07D 307/12
See application file for complete search history.

(56) References Cited

U.S. PATENT DOCUMENTS 3,256,254 A * 6/1966 Reinhardt ..................... 526/217

* cited by examiner

*Primary Examiner* — Valerie Rodriguez-Garcia
(74) *Attorney, Agent, or Firm* — William B. Miller

(57) ABSTRACT

The diallyl ether derivatives of the cis and trans stereoisomers of 2,5-bis(hydroxymethyl)tetrahydrofuran are produced. These materials are expected to be useful for making a variety of biobased polymers. Processes are further described for producing these diallyl ether derivatives in substantially quantitative yields.

11 Claims, No Drawings

DIALLYL ETHERS OF 2,5BIS(HYDROXYMETHYL)TETRAHYDROFURAN AND PROCESSES FOR MAKING THE SAME

This application is a 35 U.S.C. §371 national phase entry of International Application No. PCT/US2013/044875, filed Jun. 10, 2013, which claims priority from U.S. Provisional Patent Application 61/658,118, filed Jun. 11, 2012.

The present application claims the priority of U.S. Provisional Patent Application Ser. No. 61/658,118, filed Jun. 11, 2012 for "Diallyl Ethers of Anhydrohexitols and Processes for Making the Same", and is in the field of art relating to cyclic bifunctional materials useful as monomers in polymer synthesis and as intermediates generally, and to the methods by which such materials are made.

As these bifunctional materials are currently derived from increasingly scarce and costly petroleum resources, renewable source-based alternatives have been of increasing interest in recent years. Carbohydrates represent the most abundant biobased or renewable source feedstock for producing such alternative materials, but carbohydrates char easily and are generally unsuited to the high temperatures encountered in forming and processing the resultant polymer compositions. Further, compared to petroleum-based, hydrophobic aliphatic or aromatic feedstocks with a low degree of functionalization, carbohydrates such as polysaccharides are complex, overfunctionalized hydrophilic materials.

Consequently, researchers have sought to produce biobased materials that derive from carbohydrates but which are less highly functionalized, for example, 2,5-furandicarboxylic acid (FDCA), levulinic acid and isosorbide, which could either serve as monomers and co-monomers or as intermediates in the synthesis of useful biobased monomers and co-monomers.

THF glycol, or 2,5-bis(hydroxymethyltetrahydrofuran, is another example of a biobased material that has been of interest, though literature references are relatively few in number; presumably this is due at least in part to the unavailability to date on a commercial scale of the material 2,5-(hydroxymethyl)furaldehyde (HMF, also 2,5-(hydroxymethyl)-furfural) from which THF glycol and THF glycol derivatives would be prepared, though efforts have been long underway to develop a viable process for making HMF, see, e.g., US 2009/0156841 to Sanborn et al.

Turning now to those references relating to THF glycol or to derivatives of THF glycol, U.S. Pat. No. 7,393,963 to Sanborn et al. describes a method of making THF glycol from 2,5-(hydroxymethyl)furaldehyde (HMF, also 2,5-(hydroxymethyl)-furfural), ascribing utility to THF glycol as "a solvent, softener, humectant and in the synthesis of plasticizers, resins, surfactants, and agricultural chemicals", col. 4, lines 44-46, and in pharmaceutical applications, col. 4, line 47. The method in Sanborn et al. is summarized as including heating a reaction mixture comprising HMF, a solvent and a catalyst system comprising nickel and zirconium at a temperature, for a time, and at a pressure sufficient to promote the reduction of HMF to THF glycol. Sanborn et al. also summarizes U.S. Pat. No. 3,083,236 to Utne et al. as producing THF glycol mainly as a byproduct from HMF in the production of other derivatives, using copper chromite as a catalyst under high pressure (about 5000 psi, gauge), while Raney nickel and palladium on charcoal are also mentioned but require substantial residence times.

US 2013/0137863 to DeVries et al. describes making a THF glycol intermediate from HMF, wherein the THF glycol intermediate is then used to make epsilon-caprolactone and epsilon-caprolactam for polyamides production (as an alternative to caprolactone and caprolactam from benzene and/or toluene). The hydrogenation of HMF to make the THF glycol intermediate is described as carried out in a known manner, by means of hydrogen and a suitable hydrogenation catalyst, for example, a nickel catalyst, palladium, ruthenium, rhodium, platinum, iron, gold or copper chromite catalyst, col. 2, paragraphs 30 and 31. Hydrogenation in a solvent is preferred, with a hydrogen pressure of from 1 to 12 MPa (especially 5 to 10 MPa) and a temperature of 50 to 250 degrees Celsius (especially 70 to 110 degrees Celsius). THF glycol is then hydrogenated to 1,6-hexanediol, and the 1,6-hexanediol converted to caprolactone through a lactonization process.

Other references focus on uses of THF glycol and on different derivatives of THF glycol and the uses of such derivatives. For example, CA 654240 to Garber et al. describes preparing monoesters of HMF, then monoesters of THF glycol are formed by hydrogenating the monoesters of HMF. The THF glycol monoesters are contemplated for use as selective solvents, as in the separation of hydrocarbons, through varying the chain lengths of the monoesters to alter solubility in water and in hydrocarbons. US 2009/0018300 to Bloom et al. concerns the preparation of wholly biobased acrylic polymer and monomer compositions from biobased acrylic acid from glycerol, lactic acid and/or lactate esters, including acrylic polymer and monomer compositions employing diacrylate esters made from the biobased acrylic acid and carbohydrate derived diols, THF glycol being one such carbohydrate derived diol. And WO 2013/007585 to Jeol relates to biobased polyamides from biobased monomers, including 2,5-bis(aminomethyl)tetrahydrofuran deriving from THF glycol.

SUMMARY OF THE INVENTION

The present invention in one aspect concerns novel diallyl ether derivatives of THF glycol, in particular, of the cis and trans stereoisomers of 2,5-bis(hydroxymethyl)tetrahydrofuran. These diallyl ether derivatives are (2R,5S)-2,5-bis((allyloxy)methyl)tetrahydrofuran and (2S,5S)-2,5-bis((allyloxy)methyl)tetrahydrofuran. These materials are expected to be useful for making a variety of biobased polymers.

In a second aspect, the present invention relates to processes for making these diallyl ether derivatives in substantially quantitative yields.

DETAILED DESCRIPTION OF PREFERRED EMBODIMENTS

In commonly-assigned, copending U.S. Provisional Application Ser. No. 61/658,118, filed Jun. 11, 2012 for "Diallyl Ethers of Anhydrohexitols and Processes for Making the Same" (the "'118 Application"), which application is hereby incorporated by reference in its entirety, we described the preparation of the diallyl ethers of isosorbide, isomannide and isoidide by essentially the same synthetic methodology as described below for the diallyl ether derivatives of the cis and trans isomers of 2,5-bis(hydroxymethyl)tetrahydrofuran.

In the case of the diallyl ethers of these anhydrohexitols, and in contrast to the diallyl ethers from the cis and trans isomers of 2,5-bis(hydroxymethyl)tetrahydrofuran, the diallyl ether derivatives of isomannide and isosorbide had been previously reported. In Gregory et al., "Anhydrides of Polyhydric Alcohols, Part VIII, Some Alkenyl Ethers of 1:4-3:6-Dianhydromannitol and 1:4-3:6-Dianhydrosorbitol", Journal of the Chemical Society (1947), pp. 1405-1407, unsaturated ethers were prepared of isomannide and isosorbide to follow on earlier work to develop diacrylyl and dimethacrylyl esters of these same materials. By treating isomannide and isosorbide with allyl bromide and concentrated sodium hydroxide, the diallyl ethers were prepared in a reported 70% yield. These could then be polymerized. Dimethallyl ethers were also made, with poor yields of the isomannide derivative and better yields of the isosorbide derivative. Polymerization of these materials was reportedly more difficult.

We found, in the '118 Application, that by employing a different method of synthesis we could prepare the diallyl ether derivative of isoidide that had not been described by Gregory ((3R,3aS,6R,6aS)-3,6-bis(allyloxy)hexhydrofuro[3,2-b]furan) and could realize much greater yields of any of the diallyl ethers of the anhydrohexitols.

As mentioned, we have now found that the same methodology can be successfully employed to prepare diallyl ether derivatives of the cis and trans isomers of 2,5-bis(hydroxymethyl)tetrahydrofuran, and again in substantially quantitative yields. In common with the anhydrohexitols that are similarly derivatized in the prior '118 Application, the chirality of THF glycol provides an additional degree of freedom in polymer synthesis that can be exploited to develop certain properties and characteristics in polymer compositions developed from the diallyl ether derivatives. However, whereas the chiral centers of the anhydrohexitols can undergo selective Walden inversions under certain circumstances, the chiral centers of THF glycol are permanent and asymmetric. Further, the spatial geometry of the lone, saturated furan ring of THF glycol differs from that of the isohexides, which may likewise afford distinct properties and characteristics of interest in analogous polymer compositions prepared using the respective diallyl ether derivatives of the anhydrohexitols on the one hand and of the cis and trans isomers of 2,5-bis(hydroxymethyl)tetrahydrofuran on the other.

The inventive diallyl ether derivatives are prepared in one embodiment by reacting one or both of the cis and trans isomers of 2,5-bis(hydroxymethyl)tetrahydrofuran with a Brønsted base whose conjugate acid has an acid dissociation constant $pK_a$ greater than 16. Preferably, the Brønsted base has a $pK_a$ of about 18 or greater. In one embodiment, the Brønsted base is potassium t-butoxide; t-butanol, the conjugate acid of t-butoxide, has a $pK_a$ of about 18. The cis and trans isomers of 2,5-bis(hydroxymethyl)tetrahydrofuran can be prepared by any of the known methods for preparing THF glycol from HMF as described briefly above, or by replicating (or substantially so) the method of Example 1 hereafter. The HMF can be prepared by any of the known methods for obtaining HMF from biomass, but a preferred process would be as described in Patent Cooperation Treaty Application Ser. No. PCT/US2012/066708, filed Nov. 28, 2012 for "Process for Making HMF and HMF Derivatives from Sugars With Recovery of Unreacted Sugars Suitable for Direct Fermentation to Ethanol" (claiming priority from U.S. Ser. No. 61/584,900 filed Jan. 10, 2012), or as described in U.S. Provisional Application Ser. No. 61/782,539, filed Mar. 14, 2013 for "Process for Making HMF from Sugars with Reduced Byproduct Formation, and Improved Stability HMF Compositions", both of which are incorporated herein by reference.

By using a Brønsted base whose conjugate acid has an acid dissociation constant $pK_a$ greater than 16, for example, a Brønsted base such as potassium t-butoxide, formation of the nucleophilic anion intermediate is thermodynamically favored.

Moreover, while the hydroxide ion is a reasonably potent nucleophile and can be expected to produce allyl alcohol as a secondary product, t-butoxide is sterically hindered from appreciably reacting with allyl bromide when the same is subsequently added to the 2,5-bis(hydroxymethyl)tetrahydrofuran conjugate base(s)/residual potassium butoxide mixture at the temperatures contemplated by the inventive process and made possible by the selection and use of Brønsted bases such as potassium butoxide whose conjugate acids have higher acid dissociation constants.

In a preferred embodiment, the cis or trans stereoisomer or more commonly the combined cis and trans stereoisomers and the Brønsted base are reacted in a nonaqueous solvent system, in the substantial absence of water. A preferred nonaqueous solvent is dimethylformamide.

As an additional preferred feature, owing to the ready formation of the conjugate base(s) of 2,5-bis(hydroxymethyl)tetrahydrofuran in the initial combination with the Brønsted base(s), the overall process can be carried out at lower temperatures. For example, in one embodiment, the process is conducted at a reaction temperature of about 25 degrees Celsius or less. In another embodiment, the process is conducted at a reaction temperature of about 20 degrees Celsius or less.

In other embodiments, allyl bromide is added to the conjugate base(s) of the cis or trans stereoisomer or combined cis and trans stereoisomers gradually over time to reduce the availability of this reagent to react with residual Brønsted base, a less-favored (but still possible) side reaction at these reaction temperatures. In certain embodiments, for example, not more than about 13.3% percent allyl bromide is added per minute.

The present invention is further illustrated by the following example:

Example 1

Step A—Reduction of HMF to THF Glycol, cis and trans stereoisomer mixture:

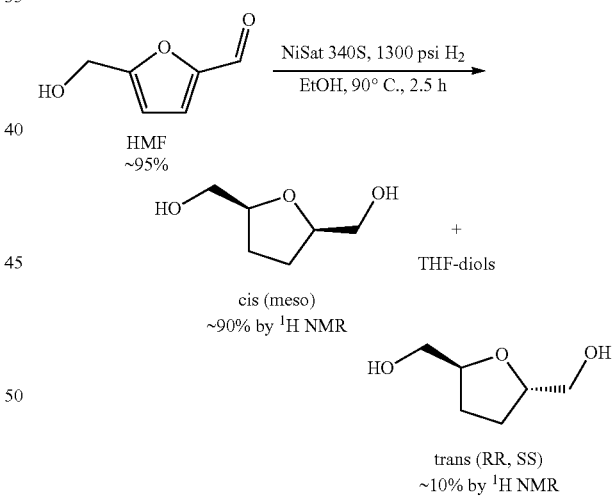

To prepare the combined cis and trans isomers of 2,5-bis(hydroxymethyl)tetrahydrofuran, a jacketed, stainless steel 1 L Parr reactor vessel was charged with 500 mL of a 30% HMF solution (about 95 percent purity) in absolute ethanol along with 15 g of NiSAT® 340 RS nickel catalyst (also sold under the tradename G-69B RS, Clariant International Ltd., having the molecular formula of "$Ni+NiO+SiO_2+ZrO_2$"). The vessel was bolted, purged three times with 1000 psi of H2, then pressurized to 1300 psi with H2, while the overhead stirrer was set to 1100 rpm. The solution was then heated to 90 degrees Celsius and the reaction monitored by $^1H$ NMR (based on disappearance of high frequency aldehyde and aromatic signals). After 2.5 hours, the reaction was deemed complete; the heterogeneous mixture was then filtered through a bed of Celite® diatomaceous earth and the filtrate was concentrated via rotary evaporation (at 60 degrees Celsius, 30 mm Hg), affording a pale yellow, viscous oil that analyzed as 80% of the mixed THF-diols (127 g retained) by HPLC (RI detection) with the absence of HMF and the intermediate furandimethanol (FDM). Vacuum distillation employing a 30 cm Vigreux column improved the purity to 98% THF-diols with a loss of about 15% of the total mass (108 g retained).

An oven dried, single neck 50 mL round bottomed flask equipped with a PTFE-coated octagonal, size ½ in.×⅜ in. stir bar was then charged with 1.10 grams of the THF-diols mixture, with 2.05 grams of potassium t-butoxide (18.3 mmol), and 25 mL of anhydrous dimethylsulfoxide (DMSO). The neck of the flask was capped with a rubber stopper affixed to argon inlet and outlet 16" needles and the flask was then immersed in a brine ice bath (at −10° C.). While stirring and under an argon blanket, 1.44 mL of allyl bromide (16.6 mmol) was added dropwise over a 10 minute period. After this time, the brine bath was removed and the reaction continued overnight. A reddish brown solution with suspended solids was observed, all of which was transferred to a 250 mL separatory funnel and diluted with 50 mL of methylene chloride and 100 mL of deionized water. Liquid-liquid extraction of the bottom organic layer with three 100 mL volumes of deionized water effectively removed the DMSO, resulting in 1.71 grams of a light yellow, loose oil after drying and concentration in vacuo (97% of theoretical yield obtained). NMR spectroscopy confirmed the existence of (2R,5S)-2,5-bis((allyloxy)methyl)tetrahydrofuran (at 90% from the cis stereoisomer) and of (2S,5S)-2,5-bis((allyloxy)methyl)tetrahydrofuran (at 10% from the trans stereoisomer): $^1$H NMR (400 MHz, CDCl$_3$) δ (ppm) 5.94 (m, 2H), 5.28 (dd, J=8.2 Hz, J=1.4 Hz, 2H), 5.24 (m, 2H), 4.03 (m, 2H), 4.00 (m, 4H), 3.50 (m, 4H), 1.95 (m, 2H), 1.71 (m, 2H); $^{13}$C NMR (125 MHz, CDCl$_3$) δ (ppm) 135.00, 117.06, 117.01, 78.69, 78.29, 73.03, 72.93, 72.50, 28.75, 28.09.

The invention claimed is:

1. (2R,5S)-2,5-bis((allyloxy)methyl)tetrahydrofuran.
2. (2S,5S)-2,5-bis((allyloxy)methyl)tetrahydrofuran.
3. A process for making a diallyl ether derivative of at least one of the cis and trans stereoisomers of 2,5-bis(hydroxymethyl)tetrahydrofuran, comprising reacting at least one of the cis and trans isomers of 2,5-bis(hydroxymethyl)tetrahydrofuran with a Brønsted base whose conjugate acid has an acid dissociation constant pK$_a$ greater than 16 to form at least one corresponding conjugate base of an isomer of 2,5-bis(hydroxymethyl)tetrahydrofuran, then reacting the conjugate base or bases so formed with allyl bromide to form the corresponding diallyl ether derivative.
4. The process according to claim 3, wherein the yield of the diallyl ether derivative or derivatives is substantially quantitative.
5. The process as in claim 3, wherein the Brønsted base is a Bronsted base whose conjugate acid has an acid dissociation constant pK$_a$ of at least about 18.
6. The process as in claim 5, wherein the Bronsted base is potassium t-butoxide and is reacted with the at least one of the cis and trans isomers of 2,5-bis(hydroxymethyl)tetrahydrofuran.
7. The process as in any one of claims 3-6, which is carried out in a nonaqueous solvent system and in the absence of water.
8. The process as in claim 7, carried out at a temperature of about 25 degrees Celsius or less.
9. The process as in claim 8, carried out at a temperature of about 20 degrees Celsius or less.
10. The process as in claim 7, wherein allyl bromide is added gradually over time.
11. The process as in claim 10, wherein not more than about 13.3 percent of the allyl bromide is added per minute.

* * * * *